United States Patent [19]

Ibrahim et al.

[11] Patent Number: 5,223,245
[45] Date of Patent: Jun. 29, 1993

[54] COLOR CHANGE MOUTHRINSE

[75] Inventors: Nader Ibrahim; Indrajit N. Desai, both of Parsippany, N.J.

[73] Assignee: Beecham Inc., Philadelphia, Pa.

[21] Appl. No.: 928,839

[22] Filed: Aug. 11, 1992

Related U.S. Application Data

[62] Division of Ser. No. 580,648, Sep. 11, 1990, Pat. No. 5,154,917.

[51] Int. Cl.⁵ ............ B65D 35/22; B65D 51/24; A61K 7/16; A61K 9/46
[52] U.S. Cl. .................... 424/7.1; 40/406; 40/407; 215/6; 215/228; 222/94; 222/95; 206/568; 424/44; 424/49; 424/57
[58] Field of Search .......... 424/7.1, 44, 49–658; 40/406, 407; 222/94, 95; 215/6, DIG. 7; 206/568

[56] References Cited

U.S. PATENT DOCUMENTS

| | | | |
|---|---|---|---|
| D. 95,772 | 5/1935 | Mondi . | |
| D. 189,938 | 3/1961 | Heintze | D58/6 |
| D. 190,101 | 4/1961 | Mangini | D58/8 |
| D. 214,549 | 7/1969 | Ledewitz | D59/18 |
| D. 287,571 | 1/1987 | Hutchins | D9/313 |
| D. 288,526 | 3/1987 | Parad | D9/341 |
| D. 290,225 | 6/1987 | Carlson | D9/341 |
| 1,112,180 | 9/1914 | Westenfelter | 424/7.1 |
| 1,717,723 | 6/1929 | McCall | 424/7.1 |
| 2,106,122 | 1/1938 | McGowan | 215/6 |
| 2,449,274 | 9/1948 | Broll | 424/7.1 |
| 2,661,870 | 12/1953 | Huenergarot | 215/6 |
| 3,197,071 | 7/1965 | Kuster | 215/6 |
| 3,337,073 | 8/1967 | Angelo | 215/6 |
| 3,518,343 | 6/1970 | Welsh et al. | 424/44 |
| 3,564,740 | 2/1971 | Calfee | 40/406 |
| 3,581,940 | 6/1971 | Cella | 222/94 |
| 3,629,468 | 12/1971 | Andersen | 424/44 |
| 3,650,831 | 3/1972 | Jungermann et al. | 134/27 |
| 3,684,120 | 8/1972 | Beeman | 215/DIG. 7 |
| 3,705,661 | 12/1972 | Davis | 215/6 |
| 3,706,149 | 12/1972 | Oliveri | 40/407 |
| 3,729,553 | 4/1973 | Gold et al. | 424/44 |
| 3,866,800 | 2/1975 | Schmitt | 222/94 |
| 3,888,976 | 6/1975 | Mlkvy et al. | 424/44 |
| 4,034,493 | 7/1977 | Ball | 40/406 |
| 4,057,921 | 11/1977 | Ball | 40/406 |
| 4,127,645 | 11/1978 | Witzel et al. | 424/44 |
| 4,132,770 | 1/1979 | Barth | 424/49 |
| 4,150,106 | 4/1979 | Assal et al. | 424/7.1 |
| 4,150,761 | 4/1979 | Collins | 215/DIG. 7 |
| 4,230,230 | 10/1980 | Mumford | 215/DIG. 7 |
| 4,273,247 | 6/1981 | Earls | 215/DIG. 7 |
| 4,323,551 | 4/1982 | Parran | 424/57 |
| 4,349,056 | 9/1982 | Heino | 215/DIG. 7 |
| 4,359,455 | 11/1962 | Nakamura et al. | 424/7.1 |
| 4,395,835 | 8/1983 | Schneider | 40/406 |
| 4,397,944 | 8/1983 | Komura et al. | 424/7.1 |
| 4,419,283 | 12/1983 | Schneider | 40/406 |
| 4,459,307 | 7/1984 | McHugh | 424/49 |
| 4,487,757 | 12/1984 | Kiozpeoplou | 424/7.1 |
| 4,566,509 | 1/1986 | Szajna | 215/DIG. 7 |
| 4,568,534 | 2/1986 | Stier et al. | 424/7.1 |
| 4,592,489 | 6/1986 | Simon et al. | 222/94 |
| 4,678,658 | 7/1987 | Casey et al. | 424/7.1 |
| 4,793,988 | 12/1988 | Casey et al. | 424/7.1 |
| 4,849,213 | 9/1989 | Schaeffer | 424/53 |
| 4,884,703 | 12/1989 | O'Meara | 215/6 |
| 4,965,063 | 10/1990 | Casey et al. | 424/7.1 |
| 5,052,590 | 10/1991 | Ratcliff | 222/94 |

FOREIGN PATENT DOCUMENTS

| 106711 | 6/1927 | Austria | 424/7.1 |
|---|---|---|---|
| 238878 | 9/1987 | European Pat. Off. | 222/94 |
| 944506 | 4/1949 | France . | |

OTHER PUBLICATIONS

Artek Company/Gene Wilensky Oct. 2, 1981 Tetra 10 Ronald Schneider (5 pp.).
Merck Index, 9th Ed. (1976) Miscellaneous Fables, Indicators, pp. MISC-94 to MISC-96 (the indicator colors are blue, brown, colorless, green, orange, pink, purple, red, violet, yellow, and mixed).
Food Chemicals Codex, Third Edition, National Academy Press (1981), pp. 568–569.

*Primary Examiner*—Shep Rose
*Attorney, Agent, or Firm*—Rosenman & Colin

[57] ABSTRACT

A mouthrinse product comprises a multi-compartment bottle with liquids of different colors stored in the compartments, the combined stream of the liquids dispensed from the bottle combining to form a liquid admixture of yet another color.

12 Claims, 3 Drawing Sheets

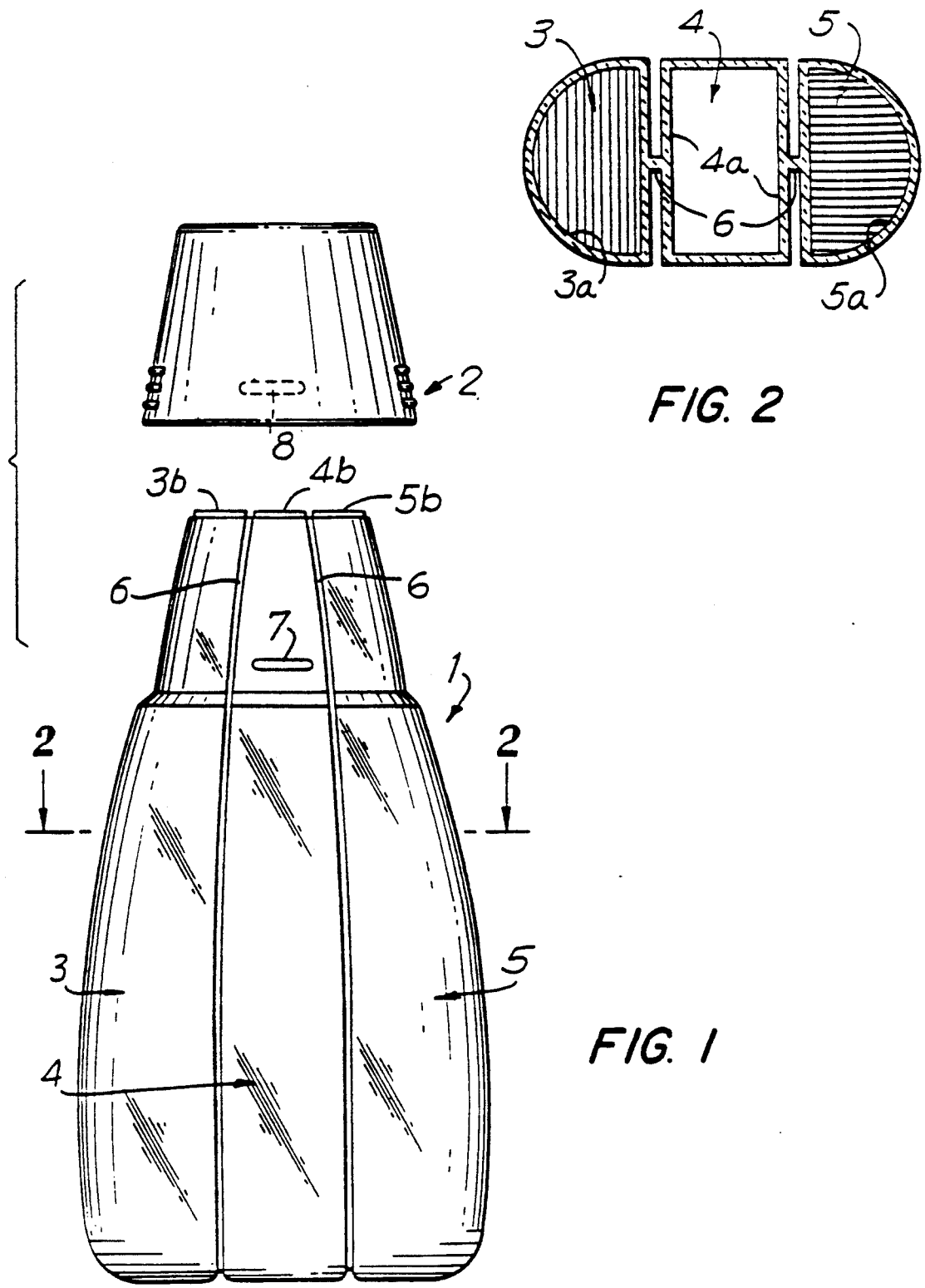

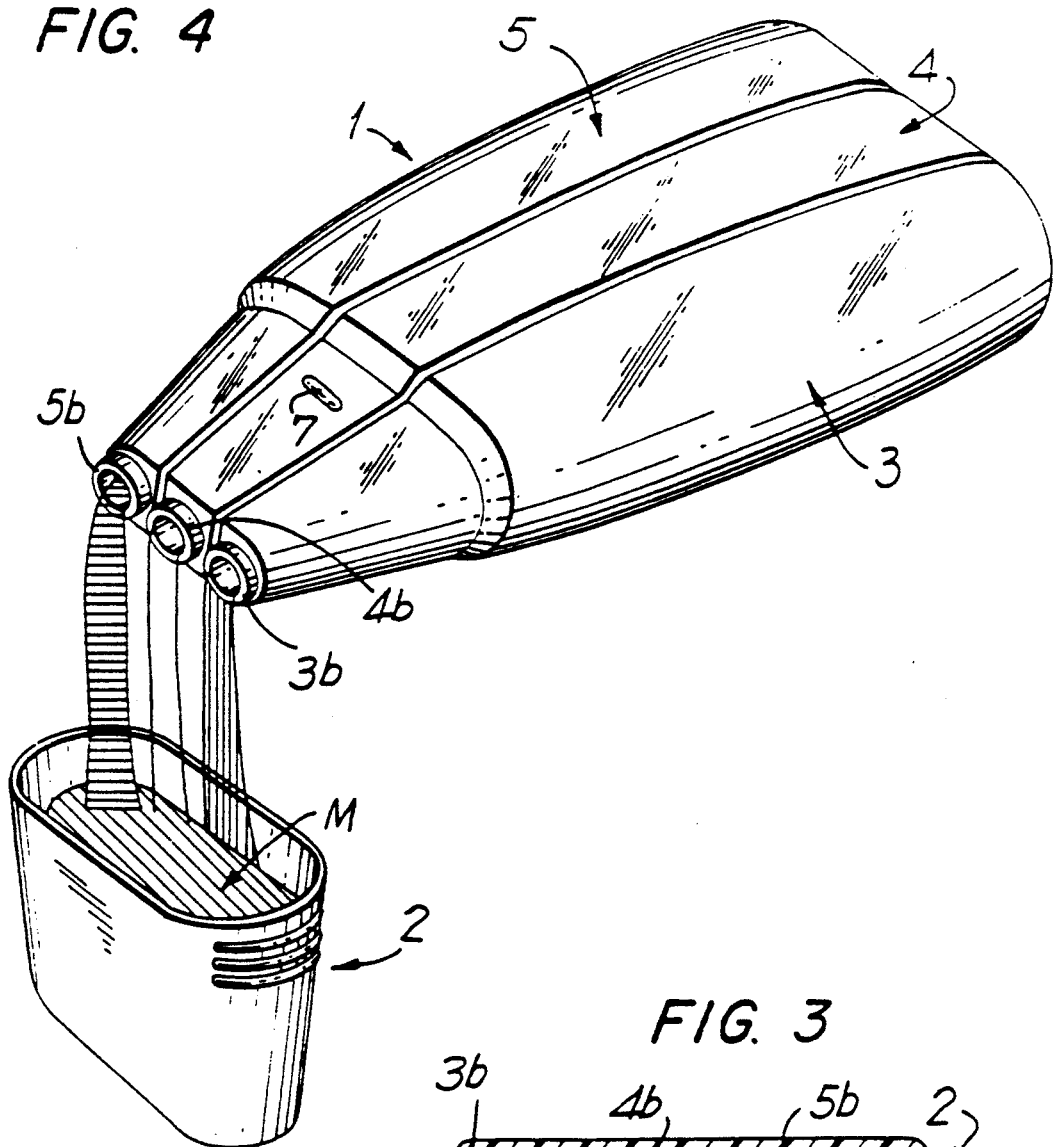
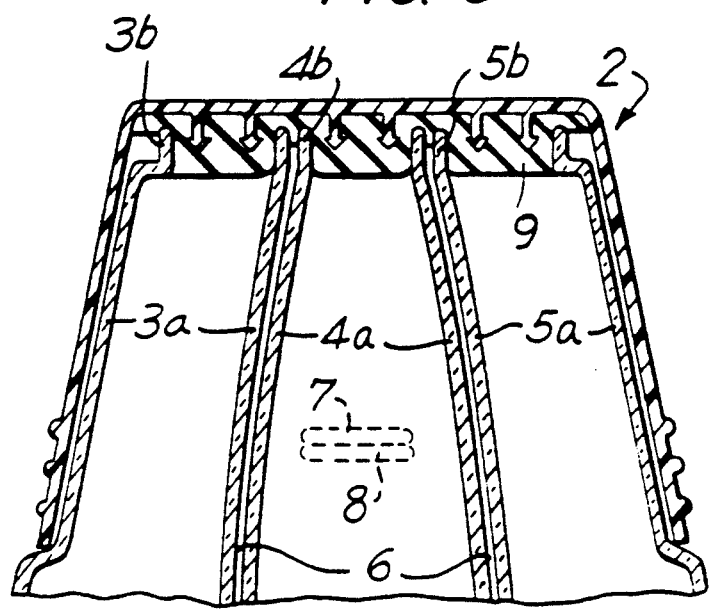

COLOR CHANGE MOUTHRINSE

CROSS-REFERENCE

This is a division of Ser. No. 580,648 filed Sep. 11, 1990, now U.S. Pat. No. 5,154,917.

The present invention relates to a mouthrinse product comprising several liquids stored in separate compartments of a multi-compartment bottle. As viewed by the consumer, the liquids in the compartments are of different colors, but when liquids are dispensed from the bottle they combine to form a liquid of yet another color.

In particular, the mouthrinse product of the invention comprises a bottle having a plurality of separate compartments each having its own open spout through which liquid stored therein may be dispensed. Each of the compartments is filled with an orally acceptable liquid, at least one of the liquids having a first color and at least another of the liquids having a second color, the liquids being out of contact with one another while they are stored in the compartments and the bottle having at least a transparent portion through which the liquids stored within the compartments may be seen. The compartments and spouts are arranged such that when the bottle is tipped from a normal vertical non-dispensing position to a dispensing position, the liquids will flow out of the compartments via the open spouts, and, after they exit the bottle, will be combined to form a liquid of a third color. Completing the mouthrinse product is a removable cap means for sealingly closing the open spouts.

In order to provide this dramatic color-change effect, the liquids having the first color are at a first pH, at least one of the other liquids is at a second pH and the dispensed liquid admixture is at a third pH; the liquids having the first color comprising an orally acceptable dye having one color at the first pH and another color at the third pH. Orally acceptable indicator dyes, such as phenolphthalein, may be used as the dye that changes color depending on pH.

Completing the mouthrinse product is a therapeutically effective amount of an oral hygiene medicament in at least one of the liquids stored in the bottle. Preferably, at least one of the liquids in the bottle comprises one part of a two-part orally acceptable effervescent couple, while at least another of the liquids comprises the other part of the effervescent couple, the two parts of the effervescent couple reacting to produce carbon dioxide when the liquids are combined after they have been dispensed from the bottle.

The present invention is illustrated in terms of its preferred embodiments in the accompanying drawings, in which:

FIG. 1 is an elevational view of a mouthrinse bottle and cap;

FIG. 2 is a view in section taken along lines 2—2 in FIG. 1;

FIG. 3 is a detail view, in section, of the cap assembled to the bottle;

FIG. 4 is a view in perspective of red, colorless and blue liquids being dispensed from the bottle and forming an aqua mouthrinse when combined;

Figure 5:
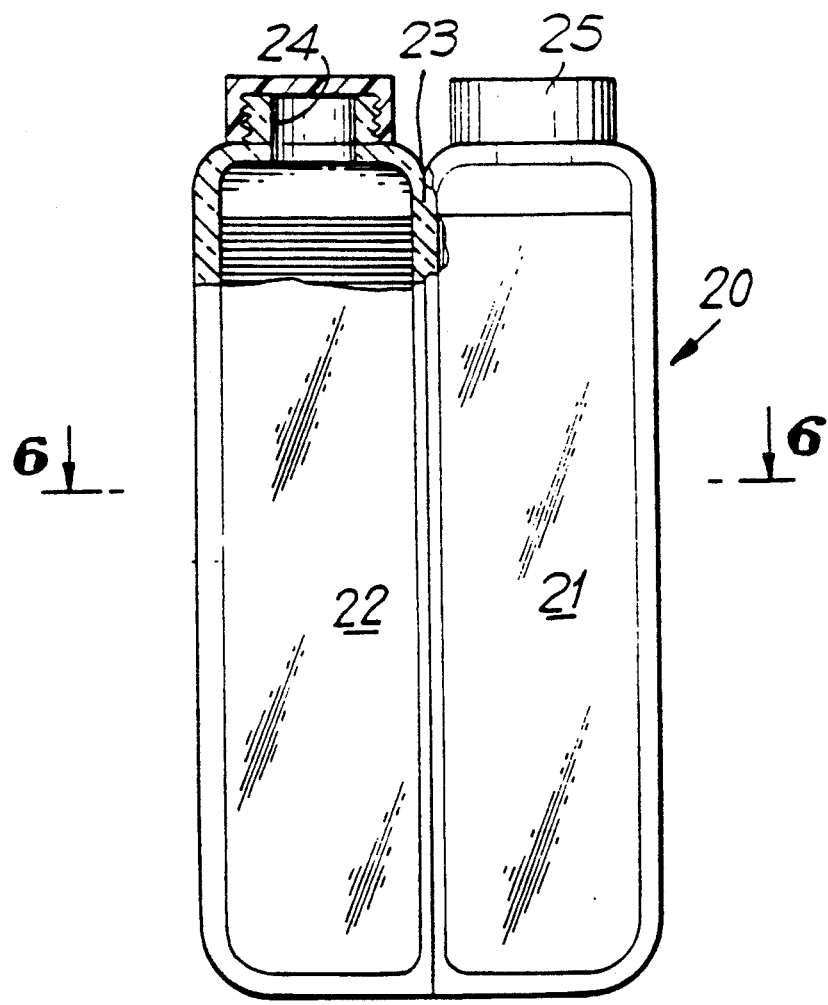
FIG. 5 is an elevational view, partly in section, of an alternative embodiment of the invention.

FIG. 1 shows a mouthrinse product of the invention comprising a bottle 1 and cap 2. Bottle 1 contains red, colorless and blue liquids in compartments 3, 4 and 5, respectively. When the bottle 1 is tipped as shown in FIG. 4, the liquids are separately dispensed from compartments 3, 4, 5 and are then combined in cap 4 to form an aqua orally acceptable mouthrinse M. The composition of the liquids will be discussed in detail hereinafter.

As best seen in FIG. 2, each of compartments 3, 4, 5, defined by its own continuous wall 3a, 4a, 5a respectively, compartment 4 being joined to compartments 3 and 5 by means of webs 6 that extend from the bottom of the bottle 1 to the spouts 3b, 4b, 5b (FIG. 3). In this manner, the liquids in compartments 3, 4, 5 are prevented from contacting one another while they are stored in the compartments.

On its front and rear surfaces, bottle 1 is provided with ribs 7 that cooperate with ribs 8 provided inside cap 2, whereby cap 2 may be snap-fitted onto bottle 1 and readily disengaged therefrom. Cap 2 is also provided with flexible gasket 9 that enters spouts 3b, 4b, 5b when cap 2 is snapped onto bottle 1, thereby sealingly closing the spouts. Preferably bottle 1 and cap 2 are each made of plastic. Conveniently, bottle 1 is formed by blow-molding, while cap 2 is injection molded. If desired, however, bottle 1 may be of glass or other suitable material, while cap 2 may be of metal, rubber or the like.

Most preferably, bottle 1 is made of a transparent material, such as a transparent plastic, so that all of the liquids stored in bottle 1 can be seen. If desired, however, only part of bottle 1 may be transparent.

Figure 6:
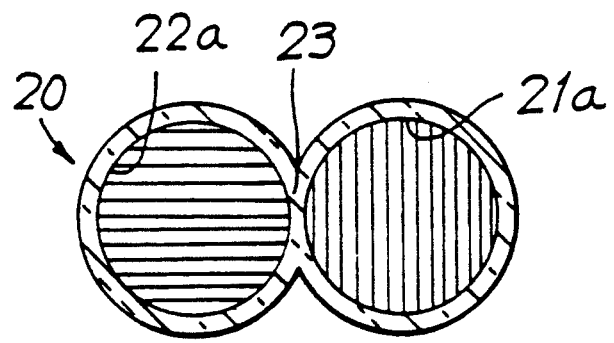
FIG. 6 is a view in section taken along lines 6—6 in FIG. 5.

While bottle 1 has three compartments, the bottle used in the present invention may have two compartments or more than three compartments. Thus, FIGS. 5 and 6 show a mouthrinse product comprising bottle 20 having compartments 21 and 22 defined by walls 21a and 22a, respectively, that are joined together via common wall 23 without any intermediate web. Compartments 21 and 22 terminate in spouts 24 to which are screw threaded caps 25 to sealingly close spouts 24. Other bottles suitable for use in the present invention include the multi-compartment bottles of U.S. Design Pat. Nos. 189,932, 190,101, 214,549, 287,571, 288,526 and 290,225 and U.S. Pat. No. 3,729,553.

Bottle 1 has a distinctive shape provided by the upwardly tapering walls 3a and 5a and by the rectangular cross-section of compartment 4 and the semi-circular cross-sections of compartments 3 and 5. However, any suitable shape may be used such as provided by the uniform, circular cross-section of compartments 21 and 22 of bottle 20.

Compartments 3, 4, 5 and 21, 22 and spouts 3b, 4b, 5b and 25 are proportioned such that the ratio of the liquids dispensed from compartments 3, 4, 5 or 21 22 to form the dispensed mouthrinse M will provide the desired reaction between the liquids and preferably will ensure that substantially all of the liquids in compartments 3, 4, 5 or 21, 22 are emptied at about the same time. It is presently preferred to provide each of compartments 3, 4, 5 and 21, 22 with substantially the same volume, whereby each compartment will contain substantially the same amount of liquid, and to provide spouts 3b, 4b, 5b or 25 with the same cross-sectional area, whereby the liquids in compartments 3, 4, 5 or 21, 22 are dispensed from the bottle 1 or 20 at substantially the same flow rate and in substantially the same amount.

In a presently preferred embodiment of the invention, compartments 3, 4, 5 contain red, colorless and blue liquids, respectively. The red liquid has an alkaline pH and contains phenolphthalein and a yellow dye, while the blue liquid contains a blue dye and the colorless water-white liquid contains no dyes. The blue and colorless liquids may both be at acid pH or one may be acidic and the other may be substantially neutral.

The red liquid is red because phenolphthalein is red at alkaline pH, the small amount of yellow dye being masked or hidden by the phenolphthalein. When bottle 1 is tipped from the vertical non-dispensing position to the dispensing position shown in FIG. 4, the liquids will flow out of compartments 3, 4, 5 and be admixed in cap 2 to form the mouthrinse M. The consumer would expect the liquids to combine to form a purple mouthrinse M. However, the liquid or liquids at acid pH will react with the red liquid to form a mouthrinse M of pH from about 5.0 to about 8.5. At a pH in the range of about 5.0 to about 8.5, the phenolphthalein in the mouthrinse M becomes colorless, and mouthrinse M is thus aqua resulting from the blue and yellow dyes in mouthrinse M, contrary to the consumer's expectation. (Of course, the liquids can be dispensed into any suitable cup or glass, if desired, rather than into cap 2.)

Compartments 21 and 22 of bottle 20 may be filled with the red and blue liquids described above, whereby after they are dispensed from bottle 20 the liquids will also combine to form an aqua mouthrinse M (not shown).

Preferably, when alkaline and acidic liquids are used, they will contain an orally acceptable base and an orally acceptable acid, respectively, as a two-part effervescent couple, so that mouthrinse M will be effervescent, resulting from carbon dioxide bubbles B formed by the reaction between the acid in the acidic liquid and the base in the alkaline liquid. Thus, the three-colored mouthrinse in bottle 1 will dispense a mouthrinse M of a fourth and different color, the effervescence being a preferred but optional feature. The consumer appeal of the product results from a unique combination of container construction and dye chemistry.

All references herein to "color" and "colors" includes colors of any hue and intensity, including black, white and colorless. Moreover, the liquids may comprise an opacifying agent, such as droplets of mineral oil, to provide a pastel effect.

While phenolphthalein is used in the above description and the following Examples, other orally acceptable indicator dyes can be used if they provide a color change at the pH of the dispensed mouthrinse, namely when at a pH in the range of from about 5.0 to about 9.0. See, for example, Food Chemical Codex, Third Edition, National Academy Press, Washington, D.C., 1981, pages 568–569, which describes orally acceptable indicator dyes. Useful orally acceptable indicator dyes include bromocresol purple (pH 5.2 yellow to pH 6.8 purple), bromothymol blue (pH 6.0 yellow to pH 7.6 blue), cresol red (pH 7.2 yellow to pH 8.8 blue), neutral red (pH 6.8 red to pH 8.0 orange), phenol red (pH 6.8 yellow to pH 8.2 red), thymol blue (pH 1.2 red to pH 8.0 yellow; pH 9.2 blue to pH 8.0 yellow).

The present invention thus provides a mouthrinse product wherein at least one of the liquids in a multi-compartment bottle contains an orally acceptable indicator dye that has different colors at different pH values and at least one of the other liquids in the bottle will provide the dispensed mouthrinse with a pH at which the indicator dye changes color. If the indicator dye, like phenolphthalein, becomes colorless, then the liquids in the compartments of the bottle may employ the "hidden" dye technique described above so that the mouthrinse M is different in color than any of the liquids in the bottle. However, where the indicator dye is not colorless when in its compartment or in the combined mouthrinse mixture, such as bromocresol purple, then it is possible to use the indicator dye as the sole dye in any of the liquids in the bottle. In such cases, two liquids can be stored in separate compartments in the bottle, one liquid containing the indicator dye and being at a first pH and the other being colorless or containing a suitable dye and being at a second pH, whereby the liquids after they are dispensed from the bottle will form a mouthrinse mixture at a third pH having a different color than any of the liquids in the bottle.

The mouthrinse of the invention will also include a therapeutically effective amount of an oral hygiene medicament. All of the liquids in the multi-compartment bottle may contain the oral hygiene medicament or the oral hygiene medicament may be in only some of the liquids. For example, if one of the liquids is at a pH that will adversely affect the oral hygiene medicament, then the medicament will be located in one of the other liquids. Any of the oral hygiene medicaments suitable for use in a mouthrinse product may be used in the present invention, such as anti-caries agents, anti-calculus agents, anti-plaque agents, anti-microbial agents or the like.

Suitable anti-caries agents include fluoride ion sources, such as alkali metal fluorides, alkali metal monofluorophosphates, stannous fluoride and the like. Preferably, an alkali metal fluoride, most preferably sodium fluoride, will be used. When employed, the anti-caries agent is used in an anti-caries effective amount. For example, fluoride ion sources may be used in an amount sufficient to provide from about 25 ppm to about 1000 ppm, preferably from about 25 to about 300 ppm fluoride, based on the total weight of the mouthrinse.

Suitable anti-calculus agents include the linear molecularly dehydrated polyphosphate salts, including alkali metal tripolyphosphates and pyrophosphates, such as sodium tripolyphosphate, di- and/or tetrasodium pyrophosphate, di- and/or tetrapotassium pyrophosphate and the like. If necessary, stabilizing agents may be used with the anti-calculus agent. Suitably, the polyphosphate anti-calculus agent may be used in an amount of up to about 5%, preferably from about 0.5 to about 2%, by weight, based on the total weight of the mouthrinse. As described in Gaffar et al U.S. Pat. No. 4,627,977, the linear polyphosphates may be used in combination with an amount of a fluoride ion source sufficient to provide about 25 to about 1000 ppm fluoride ions and about 0.005 to about 3% by weight, based on the total weight of the mouthrinse, of a synthetic anionic linear polymeric polycarboxylate having a molecular weight of from about 2000 to about one million, as inhibitors of enzymatic hydrolysis of the polyphosphate anti-calculus agent. In this connection, the fluoride ion source, when used, may serve both as an anti-caries agent and an enzyme inhibitor.

In one embodiment of the invention, the mouthrinse provides anti-calculus and anti-plaque activity, wherein the oral hygiene medicament comprises a water-soluble alkali metal tripolyphosphate salt and a substantially water-insoluble noncationic anti-bacterial agent, whereby the mouthrinse is useful in the treatment of gum disease. In such cases, one or more of the liquids in the bottle will contain an orally acceptable alcoholic solubilizing agent to solubilize the water-insoluble antibacterial noncationic agent. Useful noncationic antibacterial agents include compounds of formula (I):

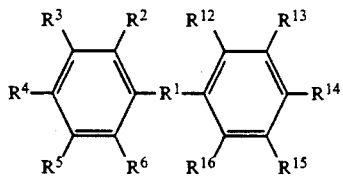

in which $R^1$ is oxygen, sulphur, or alkylene of from one to six carton atoms and each of $R^2$ to $R^6$ and $R^{12}$ to $R^{16}$ is hydrogen, hydroxyl or halogen; phenolic or bisphenolic compounds; benzoate esters; or halogenated carbanilides. Suitable compounds of formula (I) include 5,5'-dichloro-2,2'-dihydroxydiphenylmethane, 2,2'-dihydroxy-3,5,6,3',5',6'-hexachlorodiphenylmethane, 3,3'-dibrom-5,5'-dichloro-2,2'-dihydroxydiphenylether, and preferably 2,4,4'-trichloro-2'-hydroxydiphenylether (triclosan).

Examples of phenolic compounds, which include the halogenated salicylanilides, include, for example, 2-phenylphenol, 4-chlorophenol, 4-chloro-3-methylphenol, 4-chloro-3-methylphenol, 4-chloro-3,5-dimethylphenol, 2,4-dichloro-3,5-dimethylphenol, 5-methyl-2-pentylphenol, 4-isopropyl-3-methylphenol, 5-chloro-2-hydroxydiphenylmethane, 4',5-dibromosalicylanilide, 3',4',5-tribromosalicylanilide, 2,3,3',5-tetrachlorosalicylanilide, 3,3',4,5'-tetrachlorosalicylanilide, 3,5-dibromo-3'-trifluoromethylsalicylanilide, and 5-n-octanoyl-3'-trifluoromethylsalicylanilide.

Examples of bisphenolic compounds include, for example, 2,2'-methylenebis(3,4,6-trichlorophenol), 2,2'-methylenebis(4-chlorophenol), 2,2'-methylenebis(4-chloro-6-bromophenol), bis(2-hydroxy-3,5-dichlorophenyl)sulphide, and bis(2-hydroxy-5-chlorophenyl)sulphide.

Examples of benzoate esters include, for example, esters of hydroxybenzoic acid, especially the methyl, ethyl, propyl, isopropyl, butyl, isobutyl, hexyl, heptyl and benzyl esters.

Examples of halogenated carbanilides include, for example, 3,4,4'-trichlorocarbanilide, 3-trifluoromethyl-4,4'-dichlorocarbanilide, and 3,3',4-trichlorocarbanilide.

Suitably, the noncationic anti-bacterial agent will be used in an amount of from about 0.01 to about 2%, preferably about 0.05 to about 1.0%, by weight, based on the total weiqht of the mouthrinse.

Generally, the mouthrinse of the invention will comprise from about 45 to about 95%, by weight of water, based on the total weight of the mouthrinse, and the pH of the mouthrinse formed after the liquids dispensed from the bottle are combined will usually be substantially neutral, although depending on the indicator dye used, a pH of from about 5.0 to about 9.0 may be useful.

When an effervescent mouthrinse is desired, an effervescent couple is provided comprising an orally acceptable acid and an orally acceptable base, the effervescent couple reacting to produce carbon dioxide. Of course, the acid and base will be present in separate liquids stored in separate compartments to prevent premature reaction of the couple. Useful orally acceptable acids include organic acids, such as citric acid, tartaric acid, malic acid, fumaric acid and the like, while useful orally acceptable bases include metal carbonate and bicarbonate salts, such as alkali or alkaline earth metal carbonates and bicarbonates and the like. A presently preferred effervescent couple is citric acid and a sodium bicarbonate-sodium carbonate mixture. Suitably, each moiety of the effervescent couple may be present in an amount of from about 0.5 to about 6% by weight, based on the weight of the liquid containing the moiety. As is known, the larger the amount of the effervescent couple, the more gas bubbles will be produced.

Various optional conventional oral hygiene components may also be included, such as orally acceptable alcohols, excipients, detergents, buffering agents, flavoring agents, sweetening agents and the like. Preferably, the mouthrinse contains from about 1 to about 20% of glycerine, sorbitol or propylene glycol or the like to provide body and proper "mouthfeel".

Conventional manufacturing techniques are used to prepare the bottle and mouthrinse of the invention. The mouthrinse is used as described above by dispensing the liquids the bottle to form the mouthrinse and applying it to the teeth and other surfaces of the oral cavity.

The present invention is illustrated in terms of its preferred embodiments in the accompanying Examples. All parts and percentages referred to in this specification and the appended claims are by weight based upon the total weight of the mouthrinse, unless otherwise specified.

EXAMPLE 1

Red, blue and colorless liquids were prepared by admixing the following ingredients:

| INGREDIENTS | RED LIQUID | BLUE LIQUID | COLORLESS LIQUID |
| --- | --- | --- | --- |
| Deionized Water | 67.224 | 74.0689 | 71.230 |
| Ethanol, 190 Proof | 14.480 | 12.5000 | 12.500 |
| Glycerin | 12.000 | 12.0000 | 12.000 |
| Sodium Bicarbonate | 2.190 | — | — |
| Sodium Carbonate | 2.800 | — | — |
| Citric Acid | — | — | 2.900 |
| Nonionic Surfactant | 1.000 | 1.0000 | 1.000 |
| Phenolphthalein | 0.020 | — | — |
| Sodium Citrate | — | — | 0.010 |
| Cetylpyridinium Chloride | — | 0.0750 | 0.075 |
| Sodium Saccharin | 0.035 | 0.0350 | 0.035 |
| Flavor | 0.250 | 0.2500 | 0.250 |
| FD&C Blue #1 | — | 0.0022 | — |
| FD&C Yellow #5 | 0.001 | — | — |
| Disodium Hydrogen Phosphate | — | 0.0100 | — |
| Monosodium Dihyrogen Phosphate | — | 0.0600 | — |
| | 100.000% | 100.0000% | 100.000% |

The pH of the red liquid was 10.0, the pH of the colorless liquid was 2.5, and the pH of the blue liquid was 4.5. Equal amounts of the three liquids, were filled into compartments 3, 4, 5 of 18 ounce bottles of the type shown in FIGS. 1-4. The liquids after being dispensed from the bottle combined to form an effervescent antiplaque mouthrinse having a pH of 6.7 and an aqua color. The effervescence was produced by carbon dioxide bubbles formed by the reaction of sodium bicarbonate and sodium carbonate in the red liquid and citric acid in the colorless liquid.

Similar results are obtained using bottles of 12, 24 and 32 ounce capacity.

EXAMPLE 2

Red and blue liquids were prepared by admixing the following ingredients:

| INGREDIENTS | RED LIQUID | BLUE LIQUID |
| --- | --- | --- |
| DEIONIZED WATER | 69.8744 | 72.1742 |
| ETHANOL, 190 PROOF | 13.5000 | 12.5000 |
| GLYCERIN | 12.0000 | 12.0000 |
| SODIUM BICARBONATE | 1.4600 | — |
| SODIUM CARBONATE | 1.8666 | — |
| CITRIC ACID | — | 1.9334 |
| NONIONIC SURFACTANT | 1.0000 | 1.0000 |
| PHENOLPHTHALEIN | 0.0134 | — |
| SODIUM CITRATE | — | 0.0066 |
| CETYLPYRIDINIUM CHLORIDE | — | 0.1000 |
| SODIUM SACCHARIN | 0.0350 | 0.0350 |
| FLAVOR | 0.2500 | 0.2500 |
| FD&C BLUE #1 | — | 0.0008 |
| FD&C YELLOW #5 | 0.0006 | — |
|  | 100.0000% | 100.0000% |

The red liquid had a pH of 10.0 while the blue liquid had a pH of 2.5. When mixed together, the liquids formed an aqua effervescent, anti-plaque mouthrinse having a pH of 7.0.

Substantially equal amounts of the blue and red liquids of this Example 2 are filled into the compartments of the two-compartment bottle shown in FIGS. 5 and 6 to provide an 18 ounce mouthrinse product of the invention.

EXAMPLE 3

Red and blue liquids are prepared by admixing the following ingredients to obtain a red alkaline liquid and an acidic blue liquid, which when mixed together form an aqua, effervescent mouthrinse having anti-caries, anti-calculus and anti-plaque activity.

| INGREDIENTS | RED LIQUID | BLUE LIQUID |
| --- | --- | --- |
| Ethanol, 190 proof | 13.000 | 13.000 |
| Glycerin | 12.000 | 12.000 |
| Sodium Bicarbonate | 1.500 | — |
| Sodium Carbonate | 1.900 | — |
| Citric Acid | — | 1.900 |
| Nonionic Surfactant | 1.000 | 1.000 |
| Phenolphthalein | 0.010 | — |
| Sodium Citrate | — | 0.010 |
| Sodium Fluoride | 0.050 | 0.050 |
| Triclosan | 0.020 | 0.020 |
| Sodium Tripolyphosphate (Food Grade) | 1.500 | — |
| Flavor | 0.250 | 0.250 |
| FD&C Blue #1 | — | 0.001 |
| FD&C Yellow #5 | 0.001 | — |
| Deionized Water | q.s. to 100.000 | q.s. to 100.000 |

The red and blue liquids are filled into compartments of the two-compartment bottle shown in FIGS. 5 and 6 to provide an 18 ounce mouthrinse product of the invention.

EXAMPLE 4

Red, blue and colorless liquids were prepared by admixing the following ingredients.

| INGREDIENTS | RED LIQUID | BLUE LIQUID | COLORLESS LIQUID |
| --- | --- | --- | --- |
| Deionized Water | 71.464 | 74.4789 | 67.720 |
| Ethanol, 190 Proof | 11.490 | 10.5000 | 16.500 |
| Glycerin | 12.000 | 12.000 | 12.000 |
| Sodium Bicarbonate | 2.190 | — | — |
| Sodium Carbonate | 2.800 | — | — |
| Citric Acid | — | 2.9000 | — |
| Pluracare F-108 | — | — | 1.500 |
| Pluracare F-127 | — | — | 1.500 |
| Phenolphthalein | 0.020 | — | — |
| Sodium Citrate | — | 0.0100 | — |
| Cetylpyridinium Chloride | — | 0.0750 | 0.075 |
| Sodium Saccharin | 0.035 | 0.0350 | 0.035 |
| Flavor | — | — | 0.600 |
| Blue #1 | — | 0.0011 | — |
| Yellow #4 | 0.001 | — | — |
| Disodium Hydrogen Phosphate | — | — | 0.010 |
| Monosodium Dihydrogen Phosphate | — | — | 0.060 |
| Total | 100.000% | 100.0000% | 100.000% |

The pH of the red liquid was 10.0, the pH of the colorless liquid was 6.5 and the pH of the blue liquid was 2.5.

Equal amounts of the three liquids, were filled into compartments 3, 4, 5, of 18 ounce bottles of the type shown in FIGS. 1-4. The liquids after being dispensed from the bottle combined to form an effervescent anti-plaque mouthrinse having a pH of 6.7 and an aqua color. The effervescence was produced by carbon dioxide bubbles formed by the reaction of sodium bicarbonate and sodium carbonate in the red liquid and citric acid in the colorless liquid.

Similar results are obtained using bottles of 12, 24 and 32 ounce capacity.

This Example illustrates the formulation flexibility provided by the present invention. In this Example, all of the flavor is present in the colorless, substantially neutral phase, which permits the use of acid- or alkaline-sensitive flavors.

What is claimed is:

1. A mouthrinse product, which comprises:
   A. a bottle comprising a plurality of separate compartments each having its own open spout through which liquid stored therein may be dispensed and orally acceptable liquids filling each of said compartments, at least another of said liquids having a first color and at least one of said liquids having a second color, said liquids being out of contact with one another while they are stored in said compartments, said bottle having at least a transparent portion through which the liquids stored within said compartments may be seen; said compartments and spouts being arranged such that when the bottle is tipped from a normal vertical non-dispensing position to a dispensing position said liquids will flow out of said compartments via said spouts, and, after they exit the bottle, will be combined to form a liquid mixture of a third color; and removable cap means for sealingly closing said spouts;
   B. said liquids having said first color having a first pH, at least another of said liquids having a second pH and said dispensed liquid admixture having a third pH; said liquids having said first color comprising an orally acceptable dye having one color at said first pH and another color at said third pH; and C. a therapeutically effective amount of an oral hygiene medicament in at least one of said liquids in said bottle.

2. The mouthrinse product according to claim 1, wherein said bottle has a top and a bottom and comprises three longitudinally extending compartments each having its own spout at the top of each compartment, said first and second pH's being alkaline and acid, respectively, said first compartment storing a red liquid at alkaline pH as said liquid of said first color and comprising phenolphthalein as said orally acceptable dye, said second compartment storing said liquid of said second color and said third compartment storing a third liquid, at least one of said liquids in said second and third compartments being at acid pH.

3. The mouthrinse product according to claim 2, wherein said red liquid also comprises an orally acceptable yellow dye, said liquid in said second compartment is a blue liquid comprising an orally acceptable blue dye, said liquid in said third compartment is colorless and said liquid mixture is aqua.

4. The mouthrinse product according to claim 3, wherein said bottle is transparent and has opposed, parallel, flattened faces between said top and bottom.

5. The mouthrinse product according to claim 4, wherein each of said compartments contains substantially the same quantity of liquid stored therein and said compartments and said spouts are arranged such that said liquids are dispensed from said compartments via said spouts at substantially the same flow rate and in substantially the same amount.

6. The mouthrinse according to claim 1, wherein at least one of said liquids in said bottle comprises one part of a two-part orally acceptable effervescent couple and at least another of said liquids in said bottle comprises the other part of said effervescent couple, the two parts of said effervescent couple reacting to produce carbon dioxide when said liquids are combined to form said dispensed liquid admixture.

7. The mouthrinse product according to claim 6, wherein said effervescent couple comprises sodium bicarbonate and sodium carbonate and an orally acceptable organic acid.

8. The mouthrinse product according to claim 1, wherein said oral hygiene medicament comprises an anti-caries agent, an anti-calculus agent, an anti-plaque agent and/or an anti-microbial agent.

9. The mouthrinse product according to claim 8, wherein said oral hygiene medicament comprises a water-soluble alkali metal polyphosphate and a substantially water-insoluble noncationic anti-bacterial agent, whereby said mouthrinse product has anti-calculus and anti-plaque activity.

10. The mouthrinse product according to claim 9, wherein said water-soluble alkali metal polyphosphate is sodium tripolyphosphate.

11. The mouthrinse product according to claim 9, wherein said noncationic anti-bacterial agent is selected from the group consisting of diphenyl ether of the formula (I):

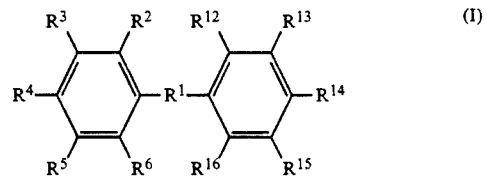

in which $R^1$ is oxygen, sulphur, or an alkylene group of from one to six carbon atoms and each of $R^2$ to $R^6$ to $R^{16}$ is hydrogen, hydroxyl or a halogen; a phenolic or bisphenolic compound; a benzoate ester and a halogenated carbanilide.

12. The mouthrinse product according to claim 11, wherein the compound of formula (I) is selected from the group consisting of 5,5'-dichloro-2,2'-dihydroxydiphenylmethane; 2,2'-dihydroxy-3,5,6,3',5',6'-hexachlorodiphenylmethane, 3,3'-dibromo-5,5'-dichloro-2,2'-dihydroxydiphenylether, and 2,4,4'-trichloro-2'-hydroxydiphenylether.

* * * * *